United States Patent [19]

Albarella et al.

[11] Patent Number: 4,810,638

[45] Date of Patent: Mar. 7, 1989

[54] ENZYME-LABELED ANTIBODY REAGENT WITH POLYALKYLENEGLYCOL LINKING GROUP

[75] Inventors: James P. Albarella, Elkhart, Ind.; Robert T. Buckler, Edwardsburg, Mich.

[73] Assignee: Miles Inc., Elkhart, Ind.

[21] Appl. No.: 888,702

[22] Filed: Jul. 24, 1986

[51] Int. Cl.[4] .......................................... G01N 33/535
[52] U.S. Cl. .......................................... 435/7; 435/14; 435/188; 436/547; 436/548; 436/512; 530/390; 530/391; 530/408; 530/409; 548/521
[58] Field of Search .......................... 435/7, 14, 188; 436/547, 548, 512; 530/390, 391, 408, 409; 548/521

[56] References Cited

U.S. PATENT DOCUMENTS 4,101,380  7/1978  Rubinstein ..................... 530/408

OTHER PUBLICATIONS

Ishikawa Journal of Immunoassay 4(3), pp. 209–227, (1983).

*Primary Examiner*—Robert J. Warden
*Assistant Examiner*—Robert Benson
*Attorney, Agent, or Firm*—Andrew L. Klawitter

[57] ABSTRACT

Enzyme-labeled antibody reagents wherein the enzyme and an antibody reagent, e.g., whole polyclonal or monoclonal antibody or a fragment thereof, are covalently linked through a bis-maleimidopolyalkyleneglycol bridge group. The reagents are useful in immunoassay and other methods for detecting an antigen or hapten that can be bound by the antibody reagent. The conjugates are highly stable and water soluble, and are characterized by a high degree of immunoreactivity and enzyme activity.

8 Claims, No Drawings

4,810,638

ENZYME-LABELED ANTIBODY REAGENT WITH POLYALKYLENEGLYCOL LINKING GROUP

BACKGROUND OF THE INVENTION

This inention relates to enzyme-labeled antibody reagents which comprise an antibody reagent, such as whole native immunoglobulin or a fragment thereof, covalently linked to an enzyme. In particular, the invention concerns a method and coupling agent for preparing such labeled reagents in which the antibody reagent and enzyme portions retain substantially their native binding and catalytic properties, respectively.

Enzyme-labeled antibody reagents have a variety of uses, principally in the detection and measurement of antigens and haptens to which the antibody reagent portion is directed, and offer a safe and convenient alternative to the use of radioisotopically-labeled antibody reagents. An important analytical use of enzyme-labeled antibody reagents is the enzyme immunoassay method. Such method, as is well known in the art, can take a variety of forms or protocols. In general, a test sample to be assayed for the presence or amount of an antigenic or haptenic analyte is combined in one or more steps with reagents that include an enzyme-labeled component which ultimately is partitioned between bound and free-forms. The enzyme activity in either of the bound and free-forms can then be measured and related to the presence or amount o.f the analyte in the test sample.

Enzyme immunoassays which require the physical separation of the bound and free-forms of the labeled reagent are referred to as heterogeneous and are exemplified by the methods described in U.S. Pat. Nos. 3,654,090; 4,016,043; and Re. 31,006. Those which can be performed without physical separation of the bound and free-forms are referred to as homogeneous and are exemplified by the descriptions in U.S. Pat. Nos. 3,817,837 and 4,043,872. Particularly useful enzyme immunoassay protocols involving the use of labeled antibody reagents are those known commonly as the immunometric and sandwich techniques.

Aside from immunoassays, enzyme-labeled antibody reagents find use in any analytical method in which a substance having antigenic or haptenic properties is detected. Such substance can be the analyte of interest or related by some indirect or intermediary assay interaction to an analyte of interest. Examples are the detection and visualization of antigens in histological and cytological samples and the detection of antigenic and haptenic labels or antigenic hybrids in nucleic acid hybridization assays. The latter assays are exemplified by the methods described in published European Patent Specification Nos. 146,039 and 163,220 commonly assigned herewith.

All of the above methods and uses of enzyme-labeled antibody reagents are dependent on the ability to conveniently and reproducibly prepare the necessary conjugates of the desired enzyme and antibody reagent components. Furthermore, critical features of the labeled reagents are the binding and catalytic properties of the conjugated antibody and enzyme portions respectively. A variety of protein-protein coupling techniques are known in the literature and many have been applied to the preparation of enzyme-labeled antibody reagents. Recent review articles in this area include those by Peters and Richards, Ann. Rev. Biochem. 47:523(1977); Das and Cox, Ann. Rev. Biophys. Bioeng. 8:165(1979); Ji, Biochem. Biophys. Acta 559:39(1979); and Conn. Meth. in Enzymol. 103:49(1983). Typical homobifunctional linking reagents include amine-to-amine coupling agents, e.g., dimethyl imidates such as dimethyl adipimidate, dimethyl malonimidate, and dimethyl suberimidate; bis-N-oxysuccinimidyl esters such as disuccinimidyl suberate (DS) and disuccinimidyl tartarate; and bis-nitrofluorobenzenes such as 1,5-difluoro-2,4-dinitrobenzene and 4,4'-difluoro-3,3'-dinitrophenylsulfone; sulfhydryl coupling agents, e.g., bis-maleimido reagents such as 1,2-phenylenedimaleimide and 1,4-phenylenedimaleimide; bis-iodoacetamides such as N,N-ethylene-bis-iodoacetamide; and bis-organomercury reagents such as 3,6-bis-(mercurimethyl)-dioxan; and the highly reactive diisothiocyanates such as 4,4'-diisothiocyano-2,2'-disulfonic acid and p-phenylenediisothiocyanate (DTIC) and aryl azides such as 4,4'-dithio-bis-phenylazide.

Heterobifunctional coupling reagents are conceptually prepared by matching the above chemically compatible reactive groups. Some common examples are 4-fluoro-3-nitrophenylazide (FNPA), N-succinimidyl-6-(4'-azido-2'-nitrophenylamino)hexanoate (SANPAH), m-maleimidobenzoyl-N-hydroxysuccinimide ester (MBS), and succinimidyl-4-(N-maleimidomethyl)-cyclohexane-1-carboxylate ester.

Common disadvantages of bifunctional reagents are their sensitivity to moisture (e.g., adipimidate, N-oxysuccinimidyl (NOS) ester, and isothiocyanate reagents) or light (phenylazides). Some reagents are poorly soluble in water, a drawback which has been overcome in the case of N-hydroxysuccinimidyl ester reagents such as DS and MBS by the preparation of the N-3-sulfosuccinimidyl ester analogs. In addition, the spacer arms of most commonly used bifunctional reagents are either too short or too lipophilic, each affecting coupling efficiency and heterology. Further, conventional amine-amine coupling reagents have the disadvantage that the antibody component is generally quite susceptible to inactivation by reagents that react with primary amines.

The coupling of proteins through hydrophilic spacer groups is reviewed by Lowe and Dean, Affinity Chromatography, J. Wiley and sons (New York 1974), Chap. 5, pp. 200–259. Descriptions of particular hydrophilic spacer arms are provided by Porath, Meth. Enzymol. 34:24-27(1974) - bis-oxirane couplers; O'Carra et al, Meth. Enzymol. 34:116-118(1974) - 1,3-diaminopropan-2-ol; and Japanese Kokai Tokkyo Koho JP No. 58,176,547 (Chem. Abstr. 100:48087u) - polyethylene glycol diamines and dihydrazides. The use of aliphatic bis-maleimides as crosslinking agents is reviewed by Lundblad and Noyes, Chemical Reagents for Protein Modification, vol. 2, CRC Press (Boca Raton, Fla. 1984), Chap. 5, pp. 129–139; with specific reagents being exemplified by those described by Japanese Kokai Tokkyo Koho JP No. 58,183,094 (Chem. Abst. 100:99096d) and JP No. 58-49,821 (Chem. Abst. 100:135441y); Cooney et al, Biochem. Pharmocol. 27(2):151-166(1978); Heilmann and Holzner, BBRC 99:1146(1981); and Sato and Nakao, J. Biochem. 90:1177(1981).

Bis-maleimides have been used to couple enzymes, including $\beta$-galactosidase, to antibody reagents [Yoshitake et al, Scand. J. Immunol. 10:81(1979)], but those that have been tried have been found to have such poor solubility in aqueous buffers that irreproducible syntheses result. There are no known attempts to use bis-maleimido polyalkyleneglycols as coupling agents for preparing enzyme-labeled antibody reagents, although such compounds are known, but have been used for completely unrelated purposes [see Japanese Kokai Tokkyo Koho JP No. 58-15,515 (Chem. Abst. 99:71625n), JP No. 58,136,637 (Chem. Abst. 100:104888v), and JP No. 58-40,374 (Chem. Abst. 99:124206k).

SUMMARY OF THE INVENTION

It has now been found that advantageous enzyme-labeled antibody reagents can be prepared by covalently linking the respective protein components through a bis-maleimidopolyalkyleneglycol bridge group linked to sulfhydryl groups of the proteins. The bridge group confers a high degree of water solubility to the resulting labeled reagents and preserves to a substantial degree the binding and catalytic properties of the antibody and enzyme portions respectively. Moreover, the synthesis of the labeled regents is significantly more reproducible than the prior art attempts using other types of bis-maleimide coupling agents.

DESCRIPTION OF THE PREFERRED EMBODIMENTS

The present enzyme-labeled antibody reagents are characterized by a bis-maleimidopolyalkylene glycol bridge group linking sulfhydryl groups in the respective enzyme and antibody portions. It will be understood that polyalkyleneglycol residues comprise those linear chains which have at least two, and preferably more, alkylene groups linked together by oxygen in the form of an ether linkage. The alkylene groups can be substituted, but preferably are unsubstituted, and can comprise any desired number of methylene units, but preferably comprises at least 2, and normally 10 or less, such units, e.g., ethylene, propylene, hexylene, and the like. The polyalkyleneglycol residue can comprise repeating alkylene units which are all the same or which vary in length and/or substitution. Any substituent off one or more alkylene units will of course be selected such that the advantageous properties of the present invention are not substantially compromised. One skilled in the art will be able to make appropriate selections. Typically such substituents could be hydroxyl, alkoxyl, or disubstituted amino moieties.

The preferred bridge group is of the formula:

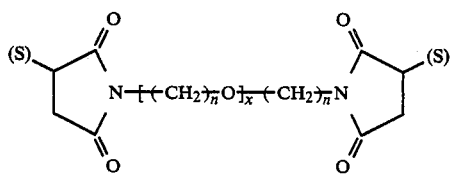

wherein (S) represents sulfhydryl groups in the antibody reagent and enzyme, respectively, to which the bridge group is covalently linked, n is an integer from 2 through 10, and x is an integer from 1 through 1000. More preferably, n wil be 6 or less, and most preferably is 2, and z will be less than about 50, more commonly less than about 20, and most preferably less than 12, with a particularly useful compound having x equal to 5. Particularly preferred bridge groups of this type will be selected from the following table:

| n | x |
|---|---|
| 2 | 2 |
| 2 | 3 |
| 2 | 5 |
| 2 | 9 |
| 2 | 11 |
| 3 | 2 |
| 3 | 3 |

Another type of useful bridge group is of the formula:

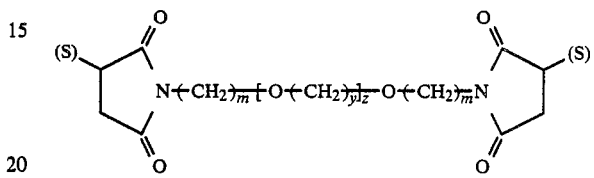

wherein (S) is as defined above, m is an integer from 2 through 10, y is an integer from 0 through 10, and z is an integer from 0 through 1000. More preferably m and y will be 6 or less, and z will be less than about 50, more commonly less than about 20, and most preferably less than 12. In these bridge groups, the polyalkyleneglycol chain is composed of an unsymmetrical number of carbon atoms. Several chains are known in the literature and are used in the preparation of polyamide and polyurethanes. Related branching chains can be prepared from the appropriate glycols either by cyanoethylation and reduction (e.g., Chem. Abstr. 49258b, Chem. Abstr. 78:111934n, and Chem. Abstr. 49:4654h) or by the tosylation/Gabriel reaction sequence. Some examples of unsymmetrical polyalkylene glycol spacer arms are those selected from the following table:

| m | y | z | reference |
|---|---|---|-----------|
| 3 | 0 | 0 | Chem. Abst. 72:101556 |
| 3 | 1 | 2 | Chem. Abst. 49:3003 |
| 3 | 2 | 2 | Chem. Abst. 72:101556 |
| 3 | 1 | 4 | Chem. Abst. 81:492586 |
| 3 | 1 | 5 | Chem. Abst. 72:101556 |

The required bis-maleimidopolyalkyleneglycol coupling agent for accomplishing the desired conjugation can be prepared by conventional synthetic means. The coupling agent for preparing labeled reagents comprising the preferred bridge group(A) can be prepared as follows.

α,ω-Diaminopolyalkyleneglycol derivatives are prepared from glycols using the chemical techniques described above. The diamines are then diacylated with maleic anhydride to give the corresponding N,N'-bis-maleamic acid intermediates. These are cyclized without isolation to the desired bis-maleimide derivatives using N-hydroxybenzotriazole and dicyclohexylcarbodiimide, as described by Trommer and Hendrick (Synthesis 1973, 484).

The antibody reagent that can be labeled with an enzyme according to the present invention can be any whole immunoglobulin or any fragment, aggregate, derivative, or modification thereof which comprises an active antibody combining site and an available sulfhydryl group for the coupling reaction. When in the form of whole immunoglobulin, it can belong to any of the classes and subclasses known, e.g., IgG, IgM, and so forth. Any fragment of such an immunoglobulin which retains specific binding affinity for its respective antigen or hapten can also be employed; for instance, the fragments of IgG conventionally referred to as Fab, Fab', and F(ab')$_2$. In addition, aggregates, polymers, derivatives, and any other chemical or other modification of such immunoglobulins or fragments can be used where appropriate.

The immunoglobulin source for the antibody reagent can be obtained in any available manner such as conventional antiserum and monoclonal techniques. Antiserum can be obtained by well-established techniques involving immunization of a host animal, such as a mouse, rabbit, guinea pig or goat, with an appropriate immunogen. Immunoglobulins can also be obtained from the secretions of hybridomas prepared by somatic cell hybridization of antibody producing lymphocytes and the like, such immunoglobulins being commonly referred to as monoclonal antibodies. The antigen or hapten to which the antibody reagent binds is obviously not critical to the present invention.

The antibody regent will of course have at least one available sulfhydryl group in order for the coupling reaction to take place. Such sulfhydryl group or groups can be present in the native antibody reagent or can be synthetically introduced. The IgG fragments Fab, Fab' and F(ab')$_2$ have available sulfhydryl groups from the reduction of disulfide bridges in the native immunoglobulin. Several methods are available in the art for introducing sulfhydryl groups to a protein, such as whole antibody, synthetically. Methods for the preparation of whole antibody-enzyme conjugates have been recently reviewed by Ishikawa and coworkers [J. Immunoassay 4:209(1983)]. In one of these methods, thiol groups are introduced onto rabbit IgG using S-acetylmercaptosuccinic anhydride. The thiol group is then deprotected and conjugated with maleimido-activated enzyme. Alternatively, rabbit IgG is reduced in the hinge region with mercaptoethylamine, treated with N-N'-o-phenylenedimaleimide, and coupled to native β-galactosidase. The converse of this procedure has also been used, i.e., coupling of reduced IgG with maleimido-activated β-galactosidase.

Essentially any enzyme can be used to label the antibody reagent according to the present invention provided that it contains an available sulfhydryl group or one can be synthetically introduced. Synthetic introduction of sulfhydryl groups can be accomplished similarly as above. Examples of just a few enzymes that can be used are horseradish peroxidase, alkaline phosphatase, and glucose oxidase. The present invention is particularly useful when the desired enzyme label is β-galactosidase because of its stability, high turnover, and ease of measurement.

The coupling of the enzyme label and the antibody reagent with the pppropriate bis-maleimidopolyalkyleneglycol coupling agent can proceed in any desired sequence of steps and under appropriately selected conditions. Normally, one of the enzyme and antibody reagents will be activated by reaction with the coupling agent, isolated from unreacted material, and then the activated component coupled to the other of the enzyme and antibody reagent. By using an appropriate excess of the material to be activated, i.e., the enzyme or antibody reagent, over the coupling agent, formation of significant intermolecularly crosslinked material can be avoided.

The activation and coupling reactions will normally be performed under mild conditions, e.g., around neutral pH and at room temperature, with moderate incubation times, e.g., an hour for the activation reaction and up to 24 hours for the coupling reaction. Conditions and incubation times can be varied widely as desired. Isolation of activated intermediate and final enzyme-labeled antibody reagent can be obtained by any desired means, usually chromatography. The bis-maleimido coupling agent can be selected from those yielding the bridge groups described hereinabove. The preferred coupling agent is of the formula:

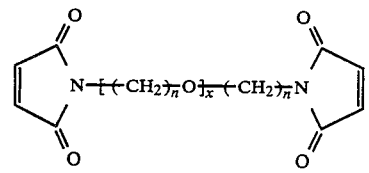

wherein n and x are as described previously.

The resulting enzyme-labeled antibody reagent will be useful in any of the analytical and other methods known in the prior art or hereafter developed. It will be particularly useful in immunoassays as described hereinabove and other methods requiring detection of a particular antigen or hapten to be assayed or which is related to an analyte of interest, e.g., nucleic acid hybridizations involving immunochemical detection of labeled probe or hybrid. The advantageous water solubility properties and high degree of immunoreactivity and enzyme activity make the present reagent particularly useful in these analytical methods.

The present invention will now be illustrated, but is not intended to be limited, by the following example.

EXAMPLE

Conjugates of β-D-galactosidase and Fab' antibody fragments were prepared and used in the detection of DNA.RNA hybrids formed in a nucleic acid hybridization assay to determine the presence of bacteria in urine.

Preparation of Bifunctional Coupling Reagent

A solution containing 2.80 g of 1,17-diamino-3,6,9,12,15-pentaoxaheptadecane (10 mmol) [Kern et al, Makromol. Chem. 180:2539(1979)] in 20 mL of dry tetrahydrofuran was added dropwise over 1 hour to a stirred solution containing 4.50 g of maleic anhydride (45 mmol) in 20 mL of tetrahydrofuran. A silty precipitate was noted during the course of the reaction. After 1 hour, the reaction mixture was filtered and the filtrate concentrated to an oil in vacuo at 50° C. (12 mm Hg followed by 0.2 mm). Obtained was 6.34 g of a crude yellow paste containing the bis-maleamic acid intermediate. This residue was then treated with 2.97 g of hydroxybenzotriazole hydrate (22 mmol) and dissolved in 20 mL of dry dimethylformamide (DMF). This solution was evaporated in vacuo. The residue was twice dissolved in 20 mL of DMF and evaporated. The residue was then placed under an inert atmosphere, dissolved in 20 mL of DMF, cooled to 0° C., and treated with 4.54 g of dicyclohexylcarbodiimide (22 mmol). The resulting mixture was stirred for 1 hour at 0° C. and then overnight at ambient temperature. The resulting dark brown mixture was filtered and concentrated to give 5.62 g of a crude, dark brown oil. The sample was purified by flash chromatography on 300 g of SiO$_2$-60 (230–400 mesh, E. M. Science, Cherry Hill, N.J., U.S.A.) using a 1% $CH_3OH-CHCl_3$ solvent mixture. Fractions containing partially purified product were pooled and concentrated to give 2.76 g of a yellow oil. The sample was flash chromatographed again on 200 g of $SiO_2$-60 using the same solvent mixture which gave the pure product [1,17-dimaleimido-3,6,9,12,15-pentaoxaheptadecane] as 1.62 g of an oil (37% yield).

Anal. Calcd. for $C_{20}H_{28}N_2O_9$: C, 54.53; H, 6.41; N, 6.36: Found: C, 54.96; H, 6.28; N, 6.48

PMR (60 MHz) $CDCl_3$ δ: 3.63 (s, 10H); 3.70 (s, 14H); 6.70 (s, 4H)

IR ($CHCl_3$) $cm^{-1}$: 2860, 1710, 1405, 1100 $cm^{-1}$

Mass Spectrum (FAB) m/e: 441 (M+1, 51%).

Conjugation of β-D-Galactosidase and an Fab' Antibody Fragment

β-Galactosidase was prepared by the method of Fowler [J. Biol. Chem. 258:14354(1983)] and stored as 50% ammonium sulfate suspension. An aliquot of enzyme suspension was centrifuged and the pellet was dissolved in 0.1 M sodium phosphate buffer, pH 7.0, 0.15 M NaCl. Dithiothreitol was added to a final concentration of 2 mM, incubated for 4 hours at 25° C., and then the mixture was chromatographed on a BioGel P6-DG column (Bio-Rad Laboratories, Richmond, Calif., U.S.A.) in 0.1 M sodium phosphate, pH 7.0, 0.15 M NaCl, 1 mM EDTA. The sulfhydryl content was 9.1–10.4 moles per mole of enzyme. Next, the reduced β-galactosidase was reacted with 200-fold molar excess of 1,17-dimaleimido-3,6,9,12,15-pentaoxaheptadecane, freshly prepared as described above in 0.1 M sodium phosphate buffer, pH 7.0, 0.15 M NaCl, 1 mM EDTA, for 1 hour at room temperature. The resulting maleimido-β-galactosidase was chromatographed on BioGel P6-DG in the same buffer and used immediately for coupling with Fab'. The maleimide content of activated β-galactosidase was determined by reaction of a portion of the derivatized enzyme with excess glutathione and then measuring the excess glutathione with Ellman's reagent [Meth. Enzymol. 25:457(1972)]. The maleimide content was 6.9–10.5 moles per mole of enzyme.

The Fab' antibody fragment was prepared as follows. Mouse monoclonal IgG to DNA.RNA hybrid was prepared as described in Boguslawski et al, J. Immunol. Meth. 89:123(1985). F(ab')$_2$ was obtained by digestion with a 1:33 weight ratio of pepsin to IgG for 16 hours at 37° C. in 0.1 M sodium acetate pH 4.2 [Lamoyi and Nisonoff, J. Immunol. Meth. 56:235 (1983)]. The digestion products were chromatographed on a Sephacryl S-200 (Pharmacia, Piscataway, N.J., U.S.A.) column in 10 mM sodium phosphate buffer, pH 6.0, 0.15 M NaCl.

A portion of the F(ab')$_2$ was labeled with dichlorotriazinylaminofluorescein (DTAF) (Sigma Chemical Co., St. Louis, Mo., U.S.A.) to be used as an antibody tracer in conjugate preparation. The labeling reaction was carried out for 1 hour in 0.1 M sodium borate buffer, pH 9.0, with 3:1 molar ratio of DTAF to F(ab')$_2$ [Blakeslee and Baines, J. Immunol. Meth. 13:305 (1976)]. The labeled antibody was separated from free DTAF on a BioGel P6-DG column. The molar DTAF/F(ab')$_2$ ratio calculated from an empirically derived formula was 2.1 [The and Feltkamp, Immunol. 18:865 (1970)].

F(ab')$_2$ was mixed with DTAF-F(ab')$_2$ in 20:1 ratio and was reduced to Fab' in 0.1 M sodium phosphate buffer, pH 7.0, 0.15 M NaCl, 1 mM EDTA, 10 mM dithiothreitol. The reduction was carried out for 3 hours at room temperature. The Fab' was isolated on BioGel P6-DG column in 0.1 M sodium phosphate, pH 7.0, 0.15 M NaCl, 1 mM EDTA and used immediately for coupling to maleimido-β-D-galactosidase prepared as described above. The sulfhydryl content of Fab' as determined by the Ellman method [Meth. Enzymol. 25:457 (1972)] was 2.5–3.0 moles sulfhydryl per mole of Fab'.

Maleimide-β-galactosidase was combined with Fab' in a 1:5 molar ratio. The final concentration of maleimido-β-galactosidase was 1.5 μM and that of Fab' was 7.5 μM. The conjugation reaction was carried out for 22 hours at 5° C. with stirring. Some aggregated material formed and was removed by centrifugation. The supernatant was chromatographed on a BioGel A-1.5 m (Bio-Rad) column in 10 mM sodium phosphate buffer, pH 6.0, 0.15 M NaCl. The fractions were examined for absorbance at 180 nm and for fluorescence of DTAF-Fab' using 492 nm excitation and 512 nm emission. The fractions showing enzyme activity and fluorescence contained conjugate and they were pooled and stored at $-15°$ C. in 0.1 M sodium phosphate, pH 7.0, 0.15 M NaCl, 0.1% $NaN_3$, 1 mg/mL bovine serum albumin (BSA), 50% glycerol. Based on the recovery of enzyme activity and fluorescence, the conjugate contained 4.1 moles Fab' per mole of enzyme.

Preparation of Nucleic Acids

Ribosomal RNA (rRNA) was prepared from *Escherichia coli* and the 16S and 23S components were separated by density gradient centrifugation [Takanami, Meth. Enzymol. 12A:491 (1967); McConkey, Meth. Enzymol. 12A:670 (1967)].

Traces of RNA in salmon sperm DNA (Pharmacia, Piscataway, N.J., U.S.A.) were degraded by incubating a solution of ~5 mg DNA/mL in 0.3 M NaOH at 37° C. for 16 hours. The solution was neutralized with 30% acetic acid and the DNA was precipitated with cold ethanol. The DNA was dissolved in 20 mM sodium phosphate, pH 7.4, 0.4 mM EDTA.

DNA probes were prepared by cloning restriction fragments containing the 23S rRNA genes from *E. coli* and *Bacillus subtilis* into M13mp18 and M13mp19 [Norrander et al, Gene 26:101 (1983)] using standard methods [Maniatis et al, Molecular Cloning. A Laboratory Manual. Cold Spring Harbor Laboratory, Cold Spring Harbor, N.Y. (1982)]. A 3.2 kilobase DNA fragment containing the *E. coli* 23S rRNA gene was obtained from pNO1301 [Jinks-Robertson et al, Cell 33:865 (1983)] by digestion with restriction endonucleases XbaI and SmaI. It was cloned into the M13 vectors which had been previously digested with XbaI and SmaI. A 1.0 kilobase DNA fragment containing two-thirds of the *B. subtilis* 23S rRNA gene was obtained from p14B1 [Stewart et al, Gene 19:153 (1982)] by digestion with restriction endonuclease BamHI and SmaI. It was cloned into the same restriction sites of M35mp18.

Bacteriophage particles were recovered from infected culture supernatants by polyethylene glycol precipitation [Yamamoto and Alberts, Virology 40:734 (1960)] and the single-stranded virion DNA was purified by phenol extraction followed by alkali treatment as above. Purified DNA was stored in 10 mM Tris.HCl, pH 6.5, 1 mM EDTA.

Immunobilization of Probe DNA on Derivatized Nylon Beads

Primary amine groups were introduced onto nylon beads (Precision Plastic Ball Co., Chicago, Ill., U.S.A.) using a modification of the method described by Morris et al, Biochem. J. 147:593 (1975). The method involves reaction of the nylon polymer with trimethyloxonium tetrafluoroborate and then with 1,6-hexanediamine. The derivatized beads contain primary amines connected to amidine groups within the polymer.

The method for derivatizing 100 nylon beads, 4.8 mm diameter, was as follows. The beads were dried thoroughly by baking in vacuo at 80° C. They were placed in a 125 mL flask with 30 mL of anhydrous methylene chloride and 0.3 g of trimethyloxonium tetrafluoroborate was added. The beads, which floated on the solvent, were stirred vigorously. The stirring also facilitated dissolution of the trimethyloxonium tetrafluoroborate, which was only partially soluble in the solvent. After 30 minutes, the beads and solvent were poured into a glass funnel which trapped the beads and allowed the solvent with undissolved trimethyloxonium tetrafluoroborate to flow out. The beads were rinsed twice with solvent and quickly placed in 30 mL of solvent containing 0.36 g of 1,6-hexanediamine. The mixture was stirred vigorously for 4 to 5 hours. The solvent was removed with a funnel as above and the beads were rinsed once with solvent and then with distilled water. The beads were shaken in three changes (500 mL each) of water at least overnight before drying in vacuo (40°–50° C.).

Aminoamidine nylon beads were placed in a round bottom flask and covered with a minimum volume of 50 mM sodium phosphate buffer, pH 7.4 containing 1.0 mM EDTA. Probe DNA was added at 2.0 μg/bead and the mixture was shaken for 6 to 8 hours at 50° C. Then 50 μg salmon sperm DNA/bead was added and the shaking at 50° C. was continued for 6 to 8 hours.

The liquid was removed from the beads and they were shaken at 55° C. for 17 hours in hybridization solution composed of four parts formamide and six parts of 10×SSPE, 0.1% (w/v) sodium dodecylsulfate (SDS), 0.1 mg/mL salmon sperm DNA and 1.0 mg/mL each of bovine albumin, polyvinylpyrrolidone and Ficoll (Pharmacia, Piscataway, N.J., U.S.A.). SSPE is 10 mM sodium phosphate buffer, pH 7.8, 0.15 M NaCl and 1 mM EDTA. Following this, the beads were rinsed twice with 0.5 mL/bead of 1×SSPE, 0.1% SDS.

Culture of Clinical Urine Samples

Quantitation of viable microorganisms in clinical urine samples was obtained by plating aliquots on tryptic soy agar with 5% sheep blood/MacConkey agar biplates (Gibco Laboratories, Grand Island, N.Y., U.S.A.) using standard calibrated inoculating loops. Plates were incubated at 37° C. for 18–24 hours.

Hybridization Assay Method

For hybridization of rRNA from bacteria in urine, 0.5 mL aliquots of urine were centrifuged and the pellets were suspended in 33 μL of 50 mM Tris-HCl buffer, pH 8.0, 1 mM EDTA, 200 μg lysozyme/mL and 25 μg lysostaphin/mL. The mixtures were incubated at 37° C. for ten minutes and then 117 μL of hybridization solution (the components of this solution were 1.28 times the concentrations given above) and an aminoamidine nylon bead with the immobilized probes were added. In experiments where purified rRNA was used, it was combined with the bead in 150 μL of 1× hybridization solution. In either case, the mixtures were shaken at 55° C. overnight, unless other times are indicated. Then the beads were washed twice at room temperature, once for 30 minutes at 55° C., and once at room temperature with 0.5 mL each of 1×SSPE, 0.1% SDS. Hybrids formed on the beads were measured by one of the immunoassay methods described below.

Beads to be assayed for DNA:RNA hybrids were shaken for 60 minutes with 150 μL of 50 mM sodium phosphate buffer, pH 7.4, 5 mg BSA/mL, 5.0 mM $MgCl_2$ and 0.5% (v/v) Tween 20 (PBMT) containing 100 ng β-galactosidase-anti-DNA:RNA conjugate. Then the solution was removed and the beads were washed three times with 0.5 mL each of PBMT containing 0.5 M NaCl. β-Galactosidase activity was measured by incubating each bead with 200 μL of 50 mM sodium phosphate buffer, pH 7.4, 5 mM $MgCl_2$ and 3 mM o-nitrophenyl-β-D-galactopyranoside for 30 minutes at 37° C. The enzyme reaction was quenched by addition of 1.8 mL of 0.1 M $Na_2CO_3$. The absorbances at 405 nm were recorded.

A hybridization time course experiment was performed using the immunoassay to determine the amount of DNA:RNA hybrid formed. Beads with immobilized probe DNA were incubated at 55° C. with 1.0 ng/bead of 23S rRNA in hybridization solution. At indicated times, beads were removed and washed. The amount of DNA:RNA hybrid formed was assayed using a monoclonal antibody to DNA:RNA hybrids and anti-mouse IgG conjugated to alkaline phosphatase. The results showed that the hybridization was complete at 15 to 20 hours.

Detection of Bacteria by Hybridization

When various levels of an *E. coli* cell lysate were hybridized with beads containing probe DNA, the immunoassay response increased linearly with the amount of lysate added. Although rRNA sequences are conserved between bacterial species, we found that rRNA probes derived from both *E. coli* and *B. subtilis* had to be used in combination to give similar sensitivities for gram-negative and gram-positive bacteria. Cultures of various bacteria commonly found in urinary tract infections were plated to determine cell counts and aliquots of lysates were tested in the hybridization assay. The results in the Table below show that the assay detected all of the species with similar sensitivities.

| SENSITIVITIES FOR DETECTION OF VARIOUS SPECIES OF BACTERIA BY HYBRIDIZATION OF 23S rRNA | |
|---|---|
| Bacterium | Absorbance (405 nm) |
| *Escherichia coli* | 0.443 |
| *Proteus mirabilis* | 0.315 |
| *Pseudomonas aeruginosa* | 0.466 |
| *Klebsiella pneumoniae* | 0.499 |
| *Morganella morganii* | 0.287 |
| *Enterobacter cloacae* | 0.436 |
| *Staphylococcus aureus* | 0.497 |
| *Staphylococcus epidermidis* | 0.458 |
| *Enterococcus sp.* | 0.436 |

Lysates of each species were hybridized at 5000 cell equivalents with the immobilized DNA probes and the immunoassay responses were determined using the β-galactosidase-anti-DNA:RNA conjugate.

The results presented above indicate that hybridization of sample 23S rRNA with immobilized DNA probes can detect relatively small numbers of bacteria; therefore, a preliminary evaluation of the method for detection of bacteriuria was undertaken. A total of 54 clinical urines were examined by hybridization and by standard culture methods using $\geq 10^4$ colony-forming units/mL as an indication of infection. Hybridization gave one false negative (1.9%) and five false positive (9.3%) results as compared to culture.

The present invention has been particularly described and exemplified above. Obviously, many modifications and variations may be made without departing from the spirit and scope hereof.

What is claimed is:

1. A water soluble enzyme-labeled antibody reagent comprising an antibody reagent and an enzyme covalently linked thereto through a bis-maleimidopolyalkyleneglycol bridge group covalently bound to sulfhydryl groups, said antibody reagent being IgG or an Fab or Fab' fragment thereof and said bridge group being of the formula:

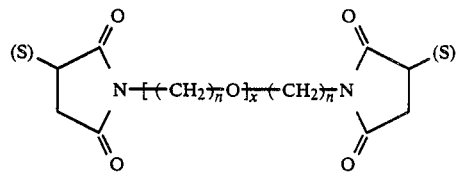

wherein (S) represents sulfhydryl groups in the antibody reagent and enzyme, respectively, to which the bridge group is covalently linked, n is an integer from 2 through 6, and x is an integer from 2 through 12.

2. The labeled reagent of claim 1 wherein n is 2.

3. The labeled reagent of claim 2 wherein x is 5.

4. The labeled reagent of claim 1 wherein the antibody reagent is an IgG Fab or Fab' fragment.

5. The labeled reagent of claim 1 wherein the enzyme is $\beta$-galactosidase.

6. The labeled reagent of claim 1 wherein said sulfhydryl groups to which the bridge group is linked are native groups in the antibody reagent and the enzyme.

7. The labeled reagent of claim 1 wherein one or both of said sulfhydryl groups to which the bridge group is linked have been synthetically introduced into the antibody reagent or the enzyme, or both.

8. The use of the enzyme-labeled antibody reagent of claim 1 in an immunoassay for detecting an antigen or hapten that can be bound by the antibody reagent.

* * * * *